US 7,470,910 B2

(12) United States Patent
Spahn

(10) Patent No.: US 7,470,910 B2
(45) Date of Patent: Dec. 30, 2008

(54) METHOD AND X RAY DETECTOR

(75) Inventor: Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/639,163

(22) Filed: Dec. 15, 2006

(65) Prior Publication Data

US 2007/0152164 A1 Jul. 5, 2007

(30) Foreign Application Priority Data

Dec. 16, 2005 (DE) .................... 10 2005 060 310

(51) Int. Cl.
*G01T 1/16* (2006.01)
(52) U.S. Cl. ................................. 250/370.09
(58) Field of Classification Search ............ 250/370.07, 250/370.09
See application file for complete search history.

(56) References Cited

U.S. PATENT DOCUMENTS

2003/0215058 A1* 11/2003 Kinno et al. ............... 378/98.8
2004/0240612 A1* 12/2004 Suzuki ........................ 378/91

* cited by examiner

*Primary Examiner*—David P Porta
*Assistant Examiner*—Marcus H Taningco
(74) *Attorney, Agent, or Firm*—Harness, Dickey & Pierce, P.L.C.

(57) ABSTRACT

In order to increase the imaging rate in the case of, in particular dynamic, X ray applications, a method for operating an X ray detector is provided. In one embodiment, the method includes applying an X radiation during an X ray time window and converting the X radiation into electric charge, storing the electric charge in storage elements of the X ray detector, reading out the electric charge, and further applying the X radiation during a further X ray time window. The further application of the X radiation is performed at least partially during the reading out of the electric charge produced from a previous application of the X radiation.

26 Claims, 4 Drawing Sheets

METHOD AND X RAY DETECTOR

PRIORITY STATEMENT

The present application hereby claims priority under 35 U.S.C. §119 on German patent application number DE 10 2005 060 310.6 filed Dec. 16, 2005, the entire contents of which is hereby incorporated herein by reference.

FIELD

Embodiments of the invention generally relate to a method for operating an X ray detector, and/or to an X ray detector.

BACKGROUND

Examples of what are known in digital X ray imaging are image intensifier camera systems based on television or CCD cameras, storage film systems with an integrated or external readout unit, systems with optical coupling of the converter foil to CCD cameras or CMOS chips, selenium-based detectors with electrostatic readout, and X ray detectors, in particular flat image detectors, with active readout matrices with direct or indirect conversion of the X radiation.

Such a detector is based on an active readout matrix, for example made from amorphous silicon (a-Si), that is precoated with an X ray converter layer or scintillator layer, for example made from cesium iodide (CsI). The incident X radiation is firstly converted into visible light in the scintillator layer. The active matrix is subdivided into a multiplicity of pixel readout units with photodiodes, which photodiodes in turn convert this light into electric charge and store it in a spatially resolved fashion on their electrode.

An active readout matrix is likewise used in the case of a so called directly converting flat image detector. However, this active readout matrix is arranged downstream of a converter layer, for example made from selenium, in which the incident X radiation is converted directly into electric charge. This charge is then stored, in turn, in the pixel readout units.

The stored electric charge is subsequently read out via an active switching element, for example a transistor, of the pixel readout unit with the aid of dedicated electronics, in order subsequently to be further processed.

The duration of the readout process together with the duration of the X ray time window, that is to say the duration of the application of the X radiation, restricts the imaging rate. The imaging rate is defined as the number of X ray pictures per time unit. Particularly in the case of dynamic X ray applications that include a sequence of many X ray pictures, however, both wide X ray time windows and high imaging rates are particularly important. Angiography and fluoroscopy, for example, are counted among the dynamic X ray applications.

SUMMARY

An embodiment of the present invention provides an X ray detector and/or a method for operating the latter that enables an increase in the imaging rate.

At least one embodiment of the invention ensures an increase in the imaging rate owing to an at least partial time overlap of the image readout process of the radiography with the X ray time window, that is to say the application of the X radiation, of the subsequent radiography. Particularly in the case of an advantageous use of the method according to at least one embodiment of the invention for dynamic X ray applications, this increase in the imaging rate leads to a shortened overall recording period or, alternatively, a substantially increased number of individual pictures per overall recording period leads to a qualitatively "better" and more accurate representation of an examination object.

On the other hand, instead of an increase in the imaging rate it is possible to select a wider X ray time window for each individual picture while ensuring an overall recording period that remains the same. The result here is likewise a more precise representation of the examination object, for example the use of a microfocus for which wide X ray time windows are required.

The X radiation is advantageously firstly converted into light, and the light is converted into electric charge via photodiodes. The electric charge is expediently stored in storage elements in the form of the photodiodes.

According to a particularly advantageous refinement of at least one embodiment of the invention, for the purpose of an inventive temporal overlap electric charge is shifted onto an additional intermediate storage element and stored there at least briefly before being read out from the known storage element. To this end, the X ray detector is designed in an advantageous way such that its pixel readout units in each case have an intermediate storage element, it being possible for the electric charge to be shifted from the storage element into the intermediate storage element, and subsequently read out. The additional intermediate storage element and/or the shifting of the electric charge onto the intermediate storage element clears the storage element, and it therefore becomes possible to use the storage element anew to store a further electric charge.

The respective electric charge, shifted into the intermediate storage element, is read out from the intermediate storage element in an advantageous way for a simple readout of the electric charge.

According to a further refinement of at least one embodiment of the invention, the storage element is reset after the shifting of the electric charge into the intermediate storage element, such that the storage element is free for renewed storage. This so-called reset can be carried out, for example, by a reset light or an electric pulse.

The further application of the X radiation is advantageously performed substantially simultaneously with the reading out of the electric charge produced from a preceding application of the X radiation. Particularly in cases where there is a comparable width of the readout time window and the X ray time window, this makes possible a substantial timesaving and/or increase in the imaging rate.

In an advantageous way for a further increase in the imaging rate, the storage of the electric charge that is produced from the X radiation applied during the further X ray time window is performed at least partially during the reading out of the electric charge produced from a previous application of the X radiation.

According to a further refinement of at least one embodiment of the invention, the intermediate storage element is designed as a storage capacitor. A storage capacitor can additionally be integrated on the pixel readout element with particular simplicity and a low outlay, and is suitable for storing an electric charge. The pixel readout units advantageously have a second switching element for easily shifting the electric charge from the storage element onto the intermediate storage element.

The method according to at least one embodiment of the invention is particularly suitable for a flat image detector, for example for a flat image detector based on amorphous, crystalline or polycrystalline silicon, or based on organic semiconductor materials.

BRIEF DESCRIPTION OF THE DRAWINGS

The invention and further advantageous refinements in accordance with further features are explained below in more detail in the drawings with the aid of schematically illustrated example embodiments, without thereby restricting the invention to these example embodiments. In the drawings.

DETAILED DESCRIPTION OF THE EXAMPLE EMBODIMENTS

Figure 1:
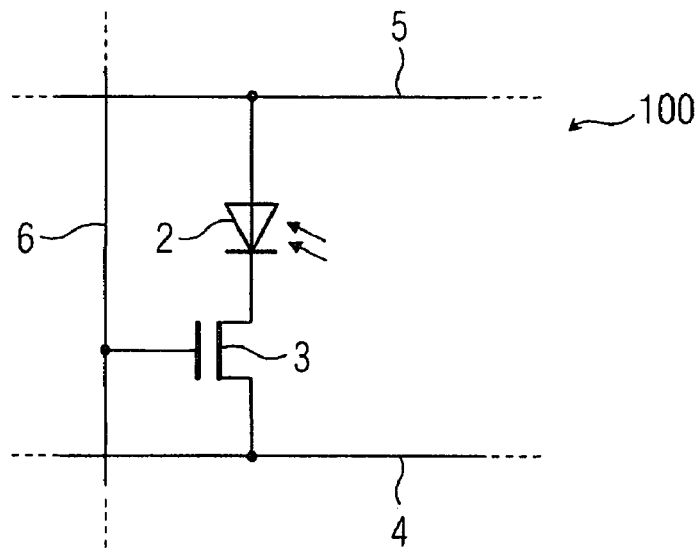
FIG. 1 shows a design of a pixel readout unit of a known X ray detector having a photodiode and switching transistor.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows the design of an individual known pixel readout element 100 that is a constituent of a pixel matrix of an X ray detector. The known pixel readout element 100 has a photodiode 2 and a switching transistor 3, for example a thin film transistor (TFT). During an X ray time window, X radiation is converted into light by means of a scintillator arranged upstream of the pixel readout unit in the direction of the X radiation. The light is then converted into electric charge by means of the photodiode 2. The electric charge is stored in a storage element, usually the photodiode 2 itself.

Arranged orthogonally to one another by pixel row or pixel column in each case are a so-called data line 4 and a gate line 6 that cover the active matrix in the form of a network. The gate line 6 is connected to the gate of the respective switching transistor 3 and serves the purpose of driving, while the data line 4 is connected to the source of the switching transistor 3 and serves for reading out the stored electric charge. Moreover, a bias line 5 is also arranged in parallel with the data line 4 and connected to the photodiode 2.

Figure 2:
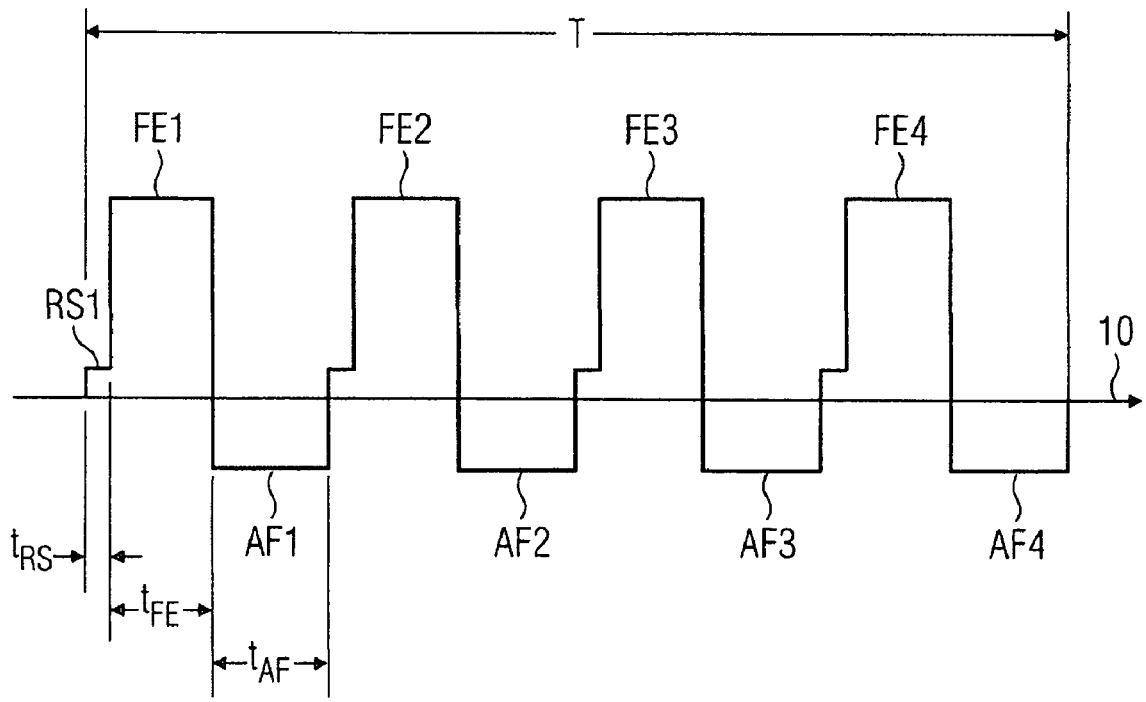
FIG. 2 shows a timing diagram of a known X ray recording cycle consisting of four X ray pictures.

FIG. 2 shows, by way of example for a dynamic X ray application, a known X ray recording cycle consisting of four X ray recordings, carried out directly in sequence, along a time axis 10. Such an X ray recording cycle usually consists of much more than four X ray recordings. A first X ray recording is composed of three parts consisting of a first reset window RS1, a first X ray time window FE1 and a first readout time window AF1.

During the first reset window RS1, the storage element is reset in such a way that it is ready for recording the storage of electric charge. During the first X ray time window FE1, an X radiation is applied, and X radiation is converted into electric charge and stored in the storage element (integration). During the first readout time window AF1, the stored charge is read out from the total pixel matrix in sequence row by row or column by column. The recording period of the first X ray recording is composed of a period $t_{FE}$ of the first X ray time window FE1, a period $t_{RS}$ of the first reset window RS1, and of a period $t_{AF}$ of the first readout time window AF1.

For the purpose of simplification, the individual periods of the time windows of a second X ray recording, a third X ray recording and a fourth X ray recording are selected in the example in accordance with the period of the time windows of the first X ray recording. Of course, this is not mandatory. The second X ray recording is composed of a second reset window RS2, a second X ray time window FE2 and a second readout time window AF2. The same holds for the third X ray recording and the fourth X ray recording. The total duration T of the X ray recording cycle, consisting of the first, the second, the third and the fourth recording, is calculated in the example embodiment represented from four times the recording duration for the first X ray recording, since no time overlaps occur between recordings. The imaging rate is yielded correspondingly from the total duration T of the X ray recording cycle divided by the number of the X ray recordings, that is to say T/4.

In the known case, the stored electric charge cannot be read out from the photodiode 2 during the period $t_{FE}$ of the respective X ray time window, that is to say while X radiation is being applied, as long as the electric charge is not completely indicated and stored. At the same time, no further X ray recording can be started during the readout process of the stored electric charge, that is to say during the readout time window, since the charge remains stored in the photodiode 2 up to which it is read out completely, in order to avoid charge losses.

Figure 3:
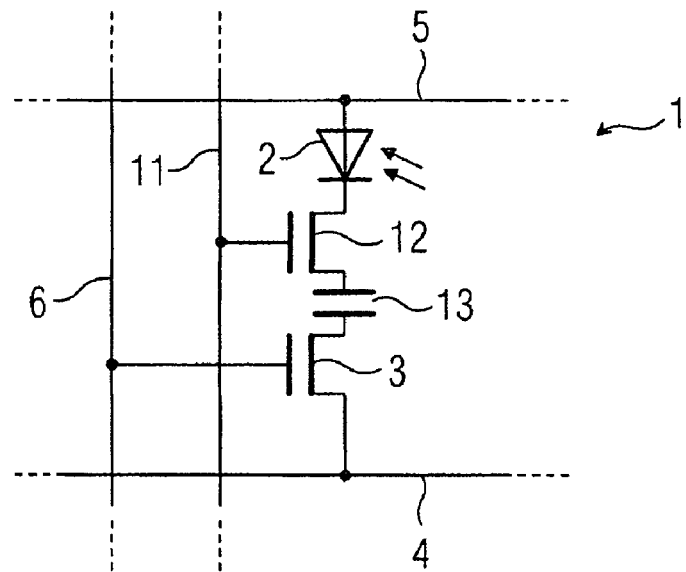
FIG. 3 shows a design of a pixel readout unit of an X ray detector according to the invention having a photodiode, switching transistor and an additional intermediate storage element.

FIG. 3 shows a pixel readout element 1 of an X ray detector according to an embodiment of the invention, in the case of which the current X ray time window and the readout time window of a previously detected electric charge can be at least partially overlapped in time. In addition to the already known components of photodiode 2, switching transistor 3, data line 4 and gate line 6, to this end the pixel readout element 1 additionally has an intermediate storage element, in particular in the form of a storage capacitor 13, and an intermediate switching element, in the form of a transfer transistor 12. According to one refinement of an embodiment of the invention, before being read out the electric charge stored in the photodiode 2 is shifted into the intermediate storage element of the X ray detector and stored there at least briefly.

The shifting of the electric charge from the storage element, for example the photodiode 2, to the intermediate storage element is performed after the ending of the storage of the electric charge on the storage element, that is to say after the X ray time window. The shifting is performed by means of the respective intermediate switching element for all pixel readout elements 1 at the same time. Arranged for this purpose in parallel with the respective gate line 6 is one transfer line 11 each, that is connected to the respective intermediate switching element. The electric charge can subsequently be read out in a known way from the respective intermediate storage elements with the aid of the intermediate switching elements in a row by row or column or column fashion.

Figure 4:
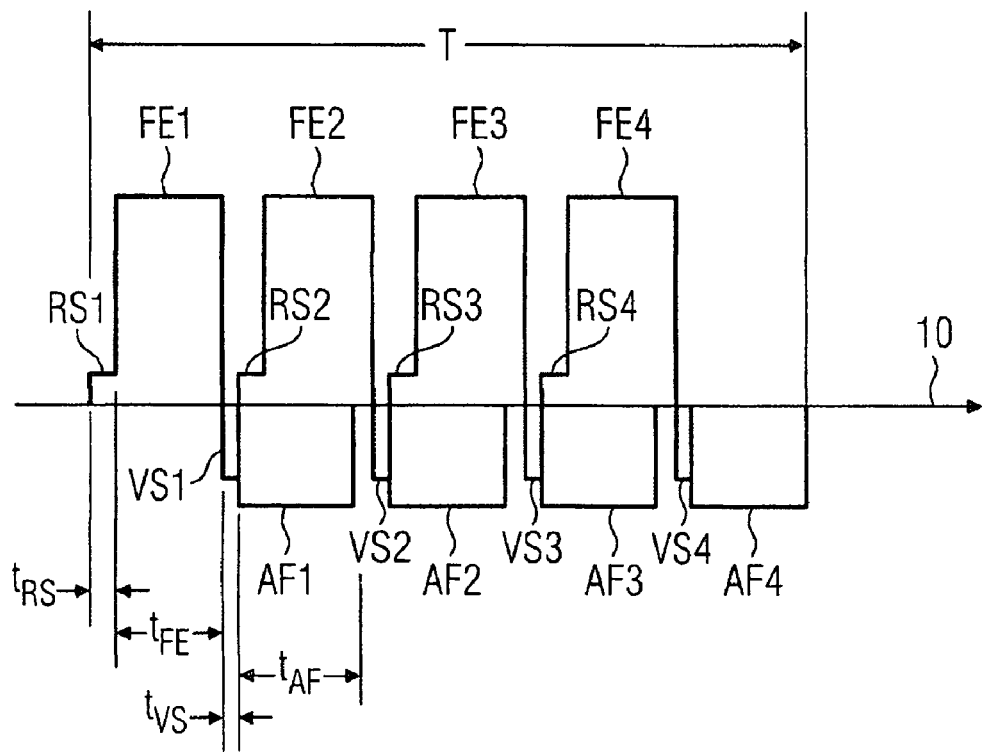
FIG. 4 shows a timing diagram of an X ray recording cycle that can be achieved using the method according to an embodiment of the invention and consists of four X ray pictures.
Figure 5:
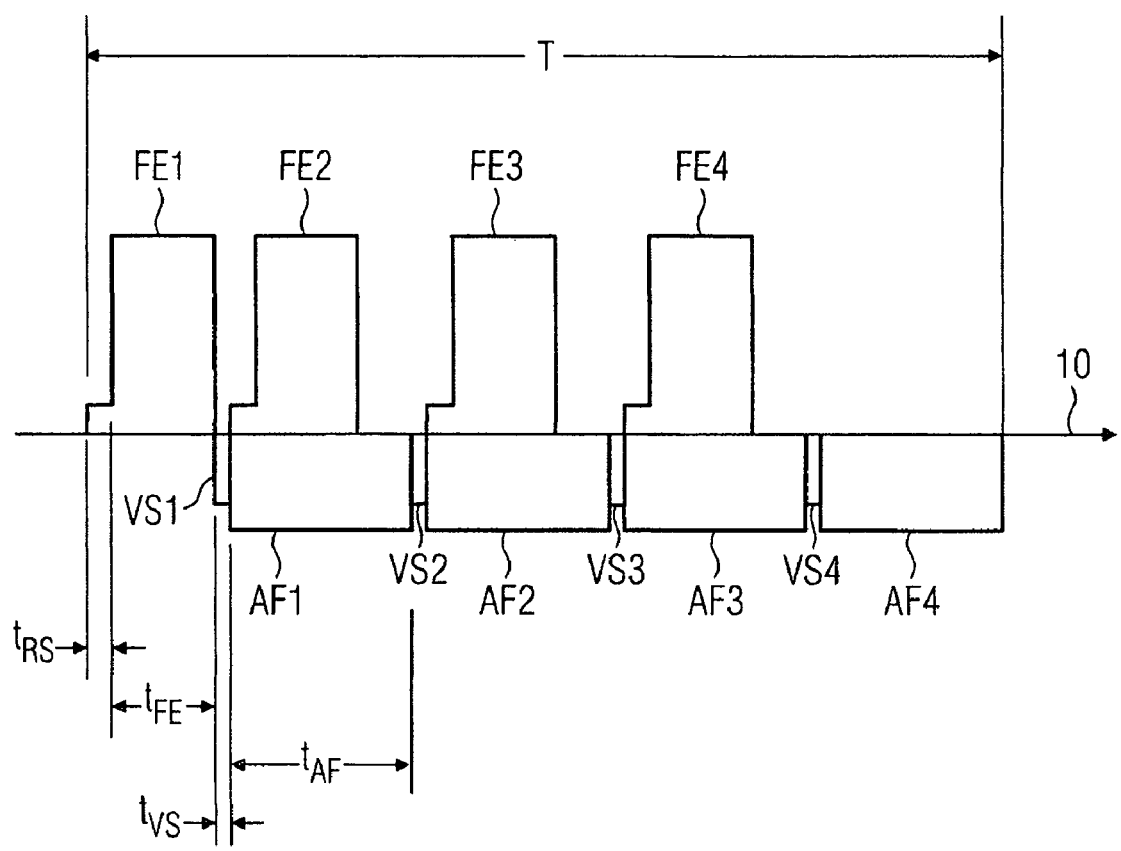
FIG. 5 shows a further timing diagram of an X ray recording cycle that can be achieved using the method according to an embodiment of the invention and consists of four X ray pictures.

FIG. 4 and FIG. 5 show two examples of X ray recording cycles that are attained by applying the method according to an embodiment of the invention. FIG. 4 and FIG. 5 likewise show four X ray recordings each, all four X ray recordings in turn having the same recording periods. The respectively first X ray recording starts with a first reset window RS1, a first X ray time window FE1 then following directly, the first shifting window VS1 following therefrom, and a first readout time window AF1 subsequently occurring. During the period $t_{VS}$ of the first shifting window VS1, the electric charge stored during the first X ray time window FE1 on the storage element, for example the photodiode 2, is shifted onto the intermediate storage element.

For each pixel readout element 1, the shifting of the electric charge from the photodiode 2 onto the intermediate storage element is independent of the remaining pixel readout elements 1 and can therefore—otherwise than the readout—take place simultaneously for all pixel readout elements 1. As a result, the period $t_{VS}$ of the first shifting window VS1 is small by comparison with the period $t_{AF}$ of the first readout time window AF1, and small by comparison with the conventional period $t_{FE}$ of the first X ray time window FE1.

After the electric charge of the first X ray recording has been shifted from the storage element onto the intermediate storage element, the storage element is reset directly thereafter in a second reset window RS2. Directly after the second reset window RS2, X radiation is then reapplied—this time in the second X ray time window FE2—and the storage element is written to anew.

The first readout time window AF1 is started directly after the end of the first shifting window VS1. This is performed in a time overlap with the second reset window RS2 and the second X ray time window FE2 following therefrom. Thus, there is a time overlap between the first readout time window AF1 and the second X ray time window FE2. Similarly, the third X ray time window FE3 and the second readout time window AF2, or the fourth X ray time window FE4 and the third readout time window AF3 are overlapped.

FIG. 4 illustrates the case in which the period $t_{FE}$ of the respective X ray time window is longer in combination with the period $t_{RS}$ of the reset window than the period $t_{AF}$ of the respective overlapping readout time window. Correspondingly, after the electric charge produced from the previous application of the X radiation has been read out, it is necessary to wait until the subsequent X ray time window is terminated before the new electric charge can be shifted from the storage element into the intermediate storage element.

FIG. 5 illustrates the case in which the period $t_{FE}$ of the respective X ray time window is shorter in combination with the period $t_{RS}$ of the reset window than the period $t_{AF}$ of the respective overlapping readout time window. Correspondingly, after the X radiation has been applied and the subsequent electric charge has been generated, it is necessary to wait until the previous electric charge has been read out before the new electric charge can be shifted from the storage element into the intermediate storage element.

The total duration T of the X ray recording cycle is calculated in the case illustrated in FIG. 4 from a sum of the individual periods $t_{RF}$ of the X ray time windows, the individual periods $t_{RS}$ of the reset windows, the individual periods $t_{VS}$ of the shifting windows and the period $t_{AF}$ of the last readout time window. In the case of a relatively large number of X ray recordings occurring in sequence, the period $t_{AF}$ of the last readout time window is negligible, and so the total duration T of the X ray recording cycle is essentially the sum of the periods $T_{RF}$ of the X ray time windows plus the sum of the periods $T_{RS}$ of the reset windows plus the sum of the periods $T_{VS}$ of the shifting windows. Thus, owing to the time overlap the total duration T is much shorter than the total duration for systems in the prior art, in the case of which all the steps are executed in sequence.

In FIG. 5, the total duration T of the X ray recording cycle is calculated from the sum of the individual periods $T_{RF}$ for the readout time windows plus the sum of the individual periods $T_{VS}$ of the shifting windows plus the period $T_{RF}$ of the first X ray time window RF1. Here, as well, the total duration T of the X ray recording cycle is much shorter than for systems in the prior art. Likewise, in both cases the imaging rate is much lower, since it is calculated from the total duration T of the X ray recording cycle divided by the number of the X ray recordings in which two cases shown in FIG. 4 and FIG. 5, that is to say T/4.

Figure 6:
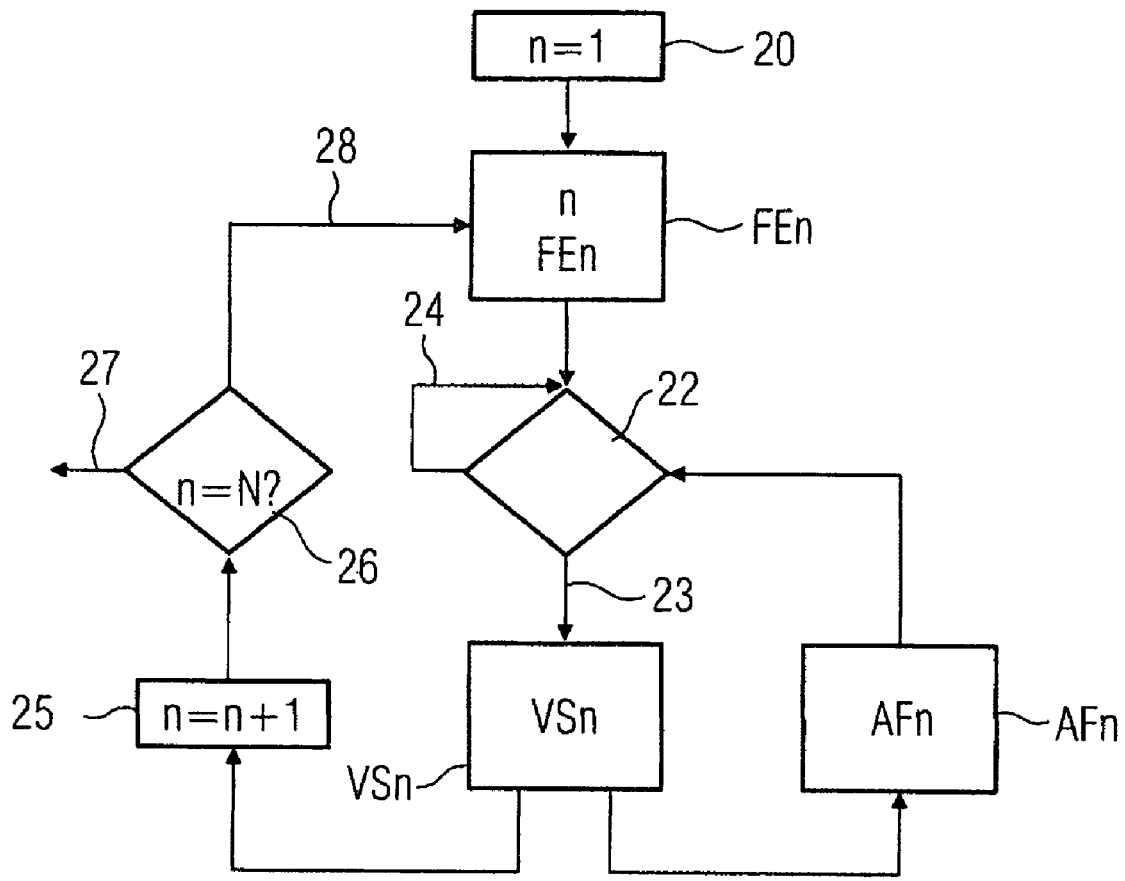
FIG. 6 shows a flowchart of a method according to an embodiment of the invention.

FIG. 6 shows a flowchart that shows the logical sequence of an X ray imaging cycle consisting of n X ray recordings. The letter n relates to the respective nth X ray recording. An input 20 starts the X ray recording cycle, which usually begins with the X ray recording n=1. There follows the nth X ray time window FEn. Subsequently, a check is made in a first branch 22 as to whether at least one of the following two conditions is fulfilled: the X ray recording is the first X ray recording of an X ray recording cycle, or the electric charge of the previous X ray recording has been completely read out. If at least one condition is fulfilled, a yes output 23 is selected. This has the consequence that the nth shifting window VSn follows.

Starting therefrom, the readout time window AFn follows. At the same time, the counter n is set high by one to n+1 in the second branch 25 and a check is subsequently made in the third branch 26 as to whether the condition for the last X ray recording (n=N) is fulfilled. If this is the case, a second yes output 27 leads to the end of the X ray recording cycle. If, by contrast, a condition for the last X ray recording n=N is not fulfilled, a second no output 28 leads to a new X ray time window RFn, which can take place in a time overlapping fashion with the readout time window of the previous X ray recording. This process is repeated until the last X ray recording n=N is carried out.

Figure 7:
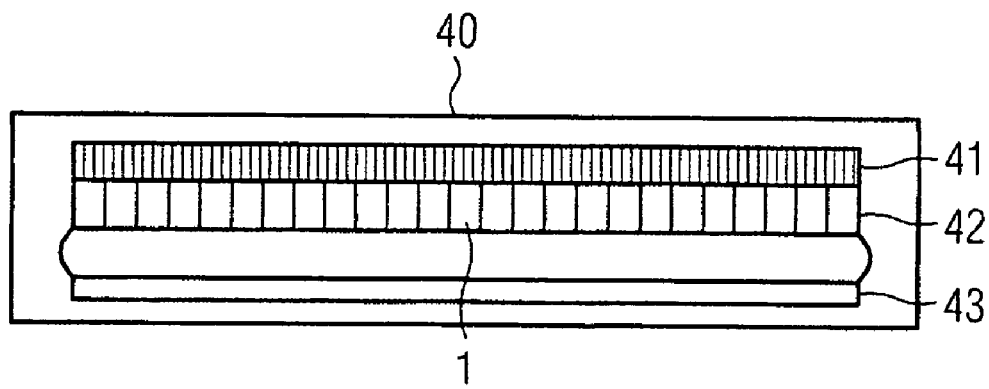
FIG. 7 shows an X ray detector according to an embodiment of the invention.

FIG. 7 shows an X ray detector 40 according to an embodiment of the invention that, in addition to a scintillator layer 41 as indirect converter and an electronic system 43, contains an active matrix 42 made from a multiplicity of pixel readout elements 1 arranged in matrix form. As illustrated in FIG. 3, the pixel readout elements 1 respectively include at least one intermediate storage element in the form of a storage capacitor 13, and an intermediate switching element in the form of a transfer transistor 12.

According to a further refinement of an embodiment of the invention, the X ray detector 40 has a direct converter for directly converting X radiation into electric charge.

At least one embodiment of the invention may be summarized briefly in the following way: in order to increase the imaging rate in the case of, in particular dynamic, X ray applications, a method for operating an X ray detector is provided and comprises the following steps: applying an X radiation during an X ray time window and converting the X radiation into electric charge, storing the electric charge in storage elements of the X ray detector, reading out the electric charge, and further applying the X radiation during a further X ray time window, the further application of the X radiation being performed at least partially during the reading out of the electric charge produced from a previous application of the X radiation.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operating an X ray detector, comprising:
    applying an X radiation during an X ray time window and converting the X radiation into electric charge;
    storing the electric charge in storage elements of the X ray detector;
    reading out the electric charge; and
    further applying the X radiation during a further X ray time window, the further application of the X radiation being performed at least partially during the reading out of the electric charge produced from a previous application of the X radiation.

2. The method as claimed in claim 1, wherein the X radiation is converted directly into electric charge.

3. The method as claimed in claim 1, wherein the X radiation is firstly converted into light, and the light is converted into electric charge by photodiodes.

4. The method as claimed in claim 3, wherein the electric charge is stored in storage elements in the form of the photodiodes.

5. The method as claimed in claim 1, wherein, before being read out from the storage element, the electric charge is shifted into an intermediate storage element of the X ray detector and stored there at least briefly.

6. The method as claimed in claim 5, wherein the electric charge is read out from the intermediate storage element.

7. The method as claimed in claim 5, wherein the storage element is reset after the shifting of the electric charge into the intermediate storage element.

8. The method as claimed in claim 1, wherein the further application of the X radiation is performed substantially simultaneously with the reading out of the electric charge produced from a preceding application of the X radiation.

9. The method as claimed in claim 6, wherein an electric charge that is produced from the X radiation applied during the further X ray time window is stored in the storage element after the shifting of the electric charge produced from the previous application of the X radiation.

10. The method as claimed in claim 8, wherein the storage of the electric charge that is produced from the X radiation applied during the further X ray time window is performed at least partially during the reading out of the electric charge produced from a previous application of the X radiation.

11. The method as claimed in claim 1, wherein the method is part of a dynamic X ray application.

12. An X ray detector for detecting an X radiation during an X ray time window having at least one further X ray time window, comprising:
    a converter, to convert X radiation into electric charge; and
    pixel readout units, arranged in matrix form, each including a storage element to store the electric charge and each including an active switching element to read out the electric charge during at least one readout time window, the further X ray time window and a readout time window in which it is possible to read out the electric charge produced from a previous detection of the X radiation being at least partially overlapped in time.

13. The X ray detector as claimed in claim 12, further comprising a direct converter to convert X radiation into electric charge.

14. The X ray detector as claimed in claim 12, further comprising an indirect converter to convert X radiation into light, and photodiodes to convert the light into electric charge.

15. The X ray detector as claimed in claim 14, wherein the pixel readout units include storage elements in the form of the photodiodes.

16. The X ray detector as claimed in claim 12, wherein the pixel readout units each include an intermediate storage element, it being possible to shift the electric charge from the storage element into the intermediate storage element and subsequently read it out.

17. The X ray detector as claimed in claim 16, wherein the intermediate storage element is designed as a storage capacitor.

18. The X ray detector as claimed in claim 12, wherein the pixel readout units include a second switching element.

19. The X ray detector as claimed in claim 12, wherein the electric charge can be read out from the intermediate storage element.

20. The X ray detector as claimed in claim 16, wherein the storage element is resetable to the intermediate storage element after the shifting of the electric charge.

21. The X ray detector as claimed in claim 12, wherein the further X ray time window and the readout time window, in which it is possible to read out the electric charge produced from a previous detection of the X radiation, are substantially completely overlapped in time.

22. The X ray detector as claimed in claim 12, wherein an electric charge producible from the X radiation detected during the further X ray time window, is storable in the storage element after the shifting of the electric charge produced from the previous detection of the X radiation.

23. The X ray detector as claimed in claim 22, wherein the storage of the electric charge is producible from the X radiation detected during the further X ray time window, is performed at least partially during the reading out of the electric charge produced from a previous detection of the X radiation.

24. The X ray detector as claimed in claim 12, wherein the X ray detector is designed as a flat image detector.

25. The X ray detector as claimed in claim 12, wherein the X ray detector is provided for dynamic X ray applications.

26. The X ray detector as claimed in claim 13, further comprising an indirect converter to convert X radiation into light, and photodiodes to convert the light into electric charge.

* * * * *